(12) United States Patent
Lim (10) Patent No.: US 8,972,012 B2
(45) Date of Patent: Mar. 3, 2015

(54) LEAD RETENTION SYSTEM FOR A PULSE GENERATOR

(75) Inventor: Wisit Lim, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 854 days.

(21) Appl. No.: 13/071,918

(22) Filed: Mar. 25, 2011

(65) Prior Publication Data

US 2012/0245657 A1 Sep. 27, 2012

(51) Int. Cl.
  *A61N 1/36* (2006.01)
  *A61N 1/375* (2006.01)
  *H01R 13/639* (2006.01)
  H01R 24/58 (2011.01)

(52) U.S. Cl.
  CPC ............ *A61N 1/3752* (2013.01); *H01R 13/639* (2013.01); *H01R 24/58* (2013.01); *H01R 2201/12* (2013.01)
  USPC .......................................................... 607/37

(58) Field of Classification Search
  CPC ...... A61N 1/3752; A61C 11/00; A61C 11/08; F21V 35/00
  USPC ............ 607/37; 439/349; 24/483–484, 20 W, 24/20 EE, 20 LS, 20 TT, 279
  See application file for complete search history.

(56) References Cited

U.S. PATENT DOCUMENTS

| | | | | |
|---|---|---|---|---|
| 1,240,654 A | * | 9/1917 | Bellodi | 431/296 |
| 4,469,104 A | * | 9/1984 | Peers-Trevarton | 607/27 |
| 5,096,327 A | * | 3/1992 | Ruland | 403/290 |
| 6,390,843 B1 | * | 5/2002 | Lim | 439/346 |
| 6,984,145 B1 | | 1/2006 | Lim | |
| 7,942,686 B2 | * | 5/2011 | Boyd et al. | 439/271 |

* cited by examiner

Primary Examiner — Mark W Bockelman (57) ABSTRACT

An implantable medical pulse generator is disclosed herein. The pulse generator is for administering electrotherapy via an implantable medical lead having a lead connector end on a proximal end of the lead. The pulse generator includes a can and a header coupled to the can. The header includes a first lead connector end receiving receptacle and a retainer configured to secure the lead connector end within the first receptacle. The retainer includes a member and a first collar, which is coaxially aligned with the first receptacle. The first collar includes an inner circumferential surface and a gap in the inner circumferential surface. The inner circumferential surface extends generally continuous and unbroken between a first face of the gap and a second face of the gap. The member is configured such that acting on the member causes a gap distance between the first face of the gap and second face of the gap to decrease, thereby reducing an inner circumferential diameter of the first collar.

13 Claims, 10 Drawing Sheets

FIG. 12

LEAD RETENTION SYSTEM FOR A PULSE GENERATOR

FIELD OF THE INVENTION

The present invention relates to medical apparatus and methods. More specifically, the present invention relates to apparatus for securing an implantable medical lead to an implantable pulse generator.

BACKGROUND OF THE INVENTION

A typical pacemaker or implantable cardioverter defibrillator ("ICD") (i.e., implantable medical pulse generator) employs a set screw and connector block arrangement to secure the lead connector ends of implantable leads in the header of the pulse generator. Such a set screw and connector block system often employs a silicone septum to insulate the metal block and set screw from body fluid. Such septum and set screw arrangements have associated shortcomings that make them less than desirable.

For example, when a torque wrench is inserted though a septum slit to access the set screw, the septum may be cored by the wrench. Such coring of the septum can result in a small piece of the septum being pushed into the set screw hex socket, the wrench then being likely to strip the hex socket of the set screw. Also, such coring can result in body fluid leaking through the septum and into contact with the metal block, causing electrical faults. Coring of the septum has been found to be a leading cause of failure or return of pulse generators.

There is a need in the art for an improved arrangement for securing lead connector ends to the header of an implantable medical pulse generator, wherein the arrangement eliminates the need for a septum at the set screw.

BRIEF SUMMARY OF THE INVENTION

An implantable medical pulse generator is disclosed herein. The pulse generator is for administering electrotherapy via an implantable medical lead having a lead connector end on a proximal end of the lead. In one embodiment, the pulse generator includes a can and a header coupled to the can. The header includes a first lead connector end receiving receptacle and a retainer configured to secure the lead connector end within the first receptacle. The retainer includes a member and a first collar, which is coaxially aligned with the first receptacle. The first collar includes an inner circumferential surface and a gap in the inner circumferential surface. The inner circumferential surface extends generally continuous and unbroken between a first face of the gap and a second face of the gap. The member is configured such that acting on the member causes a gap distance between the first face of the gap and second face of the gap to decrease, thereby reducing an inner circumferential diameter of the first collar.

Another implantable medical pulse generator is disclosed herein. In one embodiment, the pulse generator includes a can and a header coupled to the can. The header includes a first lead connector end receiving receptacle, a second lead connector end receiving receptacle, and a retainer. The retainer includes a member, a first collar, and a second collar. The first collar is coaxially aligned with the first receptacle and the second collar is coaxially aligned with the second receptacle. The first collar and the second collar are coupled together and share a common gap in an inner circumferential surface of each collar. The inner circumferential surface of each collar extends generally continuous and unbroken between a first face of the gap and a second face of the gap. The member is configured such that acting on the member causes a gap distance between the first face of the gap and second face of the gap to decrease, thereby reducing an inner circumferential diameter of each collar.

Yet another implantable medical pulse generator is disclosed herein. In one embodiment, the pulse includes a lead connector end retainer assembly, which includes a pair of adjacent collars coupled together by a middle portion in a side-by-side arrangement wherein the collars open in generally a same direction. The middle portion is divided by a gap defined by a first face and a second face opposite and spaced apart from the first face. Each collar has an inner circumferential surface extending generally continuous and unbroken between the first face of the gap and the second face of the gap. The retainer assembly further includes a member that extends across the gap and is manipulated to reduce a distance across the gap between the first face and the second face.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

A lead connector end retainer assembly 64 of an implantable medical pulse generator 20 is disclosed herein. The retainer assembly does not employ the standard setscrew-septum arrangement and, accordingly, does not suffer from the issues that accompany the standard setscrew-septum arrangement.

As discussed in detail below, in one embodiment, the lead connector end retainer assembly 64 includes a pair of adjacent collars 72 and 74 coupled together by a middle portion 76 in a side-by-side arrangement wherein the collars open in generally a same direction. The middle portion is divided by a gap 82 defined by a first face 86 and a second face 90 opposite and spaced apart from the first face. Each collar has an inner circumferential surface 104 and 106 extending generally continuous and unbroken between the first face of the gap and the second face of the gap. The retainer assembly further includes a member 66 that extends across the gap and is manipulated to reduce a distance across the gap between the first face and the second face.

Figure 1:
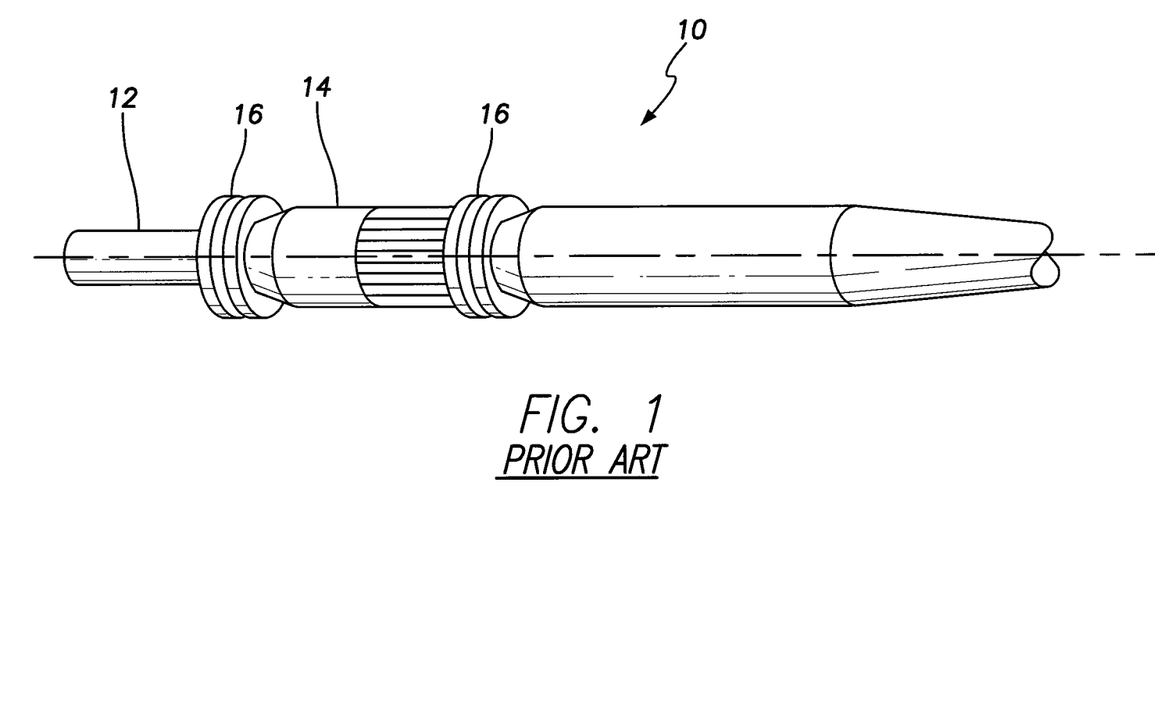
FIG. 1 is an isometric view of a proximal end portion (i.e., lead connector end) of a conventional transvenous bipolar pacing lead.

Before beginning a detailed discussion of the retainer assembly 64, a general discussion is first given regarding the features of a common lead connector end at the proximal end of an implantable medical lead followed by a general discussion of the features of an implantable medical pulse generator FIG. 1 shows a proximal end portion 10 of a conventional transvenous, bipolar pacing lead. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads having proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consist of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 conforms to the IS-1 standard, comprising a pair of coaxial spaced-apart terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead may each be engaged by a conductive garter spring contact or other resilient electrical contact element carried by a connector assembly as will be described. The proximal end portion further comprises spaced-apart pairs of seal rings 16 for preventing body fluids from reaching the electrical contacts. With the proximal end portion 10 of the lead inserted in a lead receptacle of a connector assembly, the tip and ring terminals 12 and 14 are electrically coupled via the contacts and a feedthrough to the electronic circuits within the hermetically sealed, attached cardiac pacemaker, or other implantable tissue stimulation and/or sensing device (i.e., pulse generator).

Figure 2:
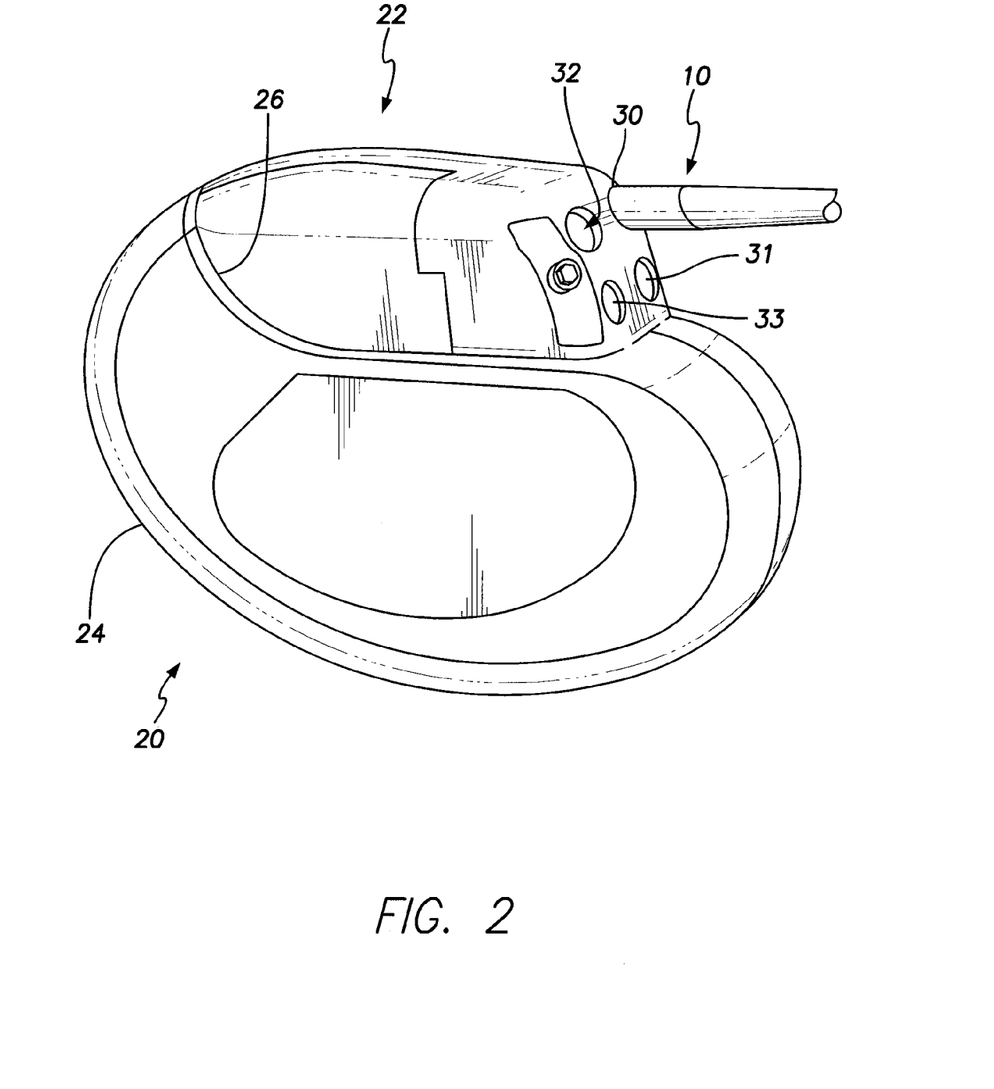
FIG. 2 is an isometric view of a multi-site or multi-chamber cardiac pacemaker/defibrillator unit (i.e., pulse generator) incorporating a connector assembly in accordance with one specific, exemplary embodiment.

FIG. 2 shows a multi-site or multi-chamber cardiac pacemaker/defibrillator unit (i.e., pulse generator) 20 incorporating a connector assembly 22 in accordance with one specific, exemplary embodiment. The cardiac pacemaker/defibrillator unit 20 is of a conventional design, including a hermetically sealed can or casing 24 enclosing the electronic components of the pacemaker/defibrillator unit with the connector assembly 22 mounted along a top edge 26 of the unit.

FIG. 2 illustrates that, in some embodiments, the connector assembly 22 may include four or more receptacles 30, 31, 32 and 33 for receiving the proximal ends of four leads. Such pulse generators 20 with four leads are sometimes referred to as bi-ventricular, bi-atrial devices, or 4×4 devices because all four chambers of the heart may be stimulated and/or sensed. FIG. 2 shows the proximal end portion 10 of a lead inserted in a receptacle 30. In other embodiments, the connector assembly 22 includes only two receptacles comprising a single pair of receptacles 30 and 31 for receiving the proximal ends of leads such as, for example, conventional bipolar leads and/or conventional cardioverting and/or defibrillating leads.

Figure 3:
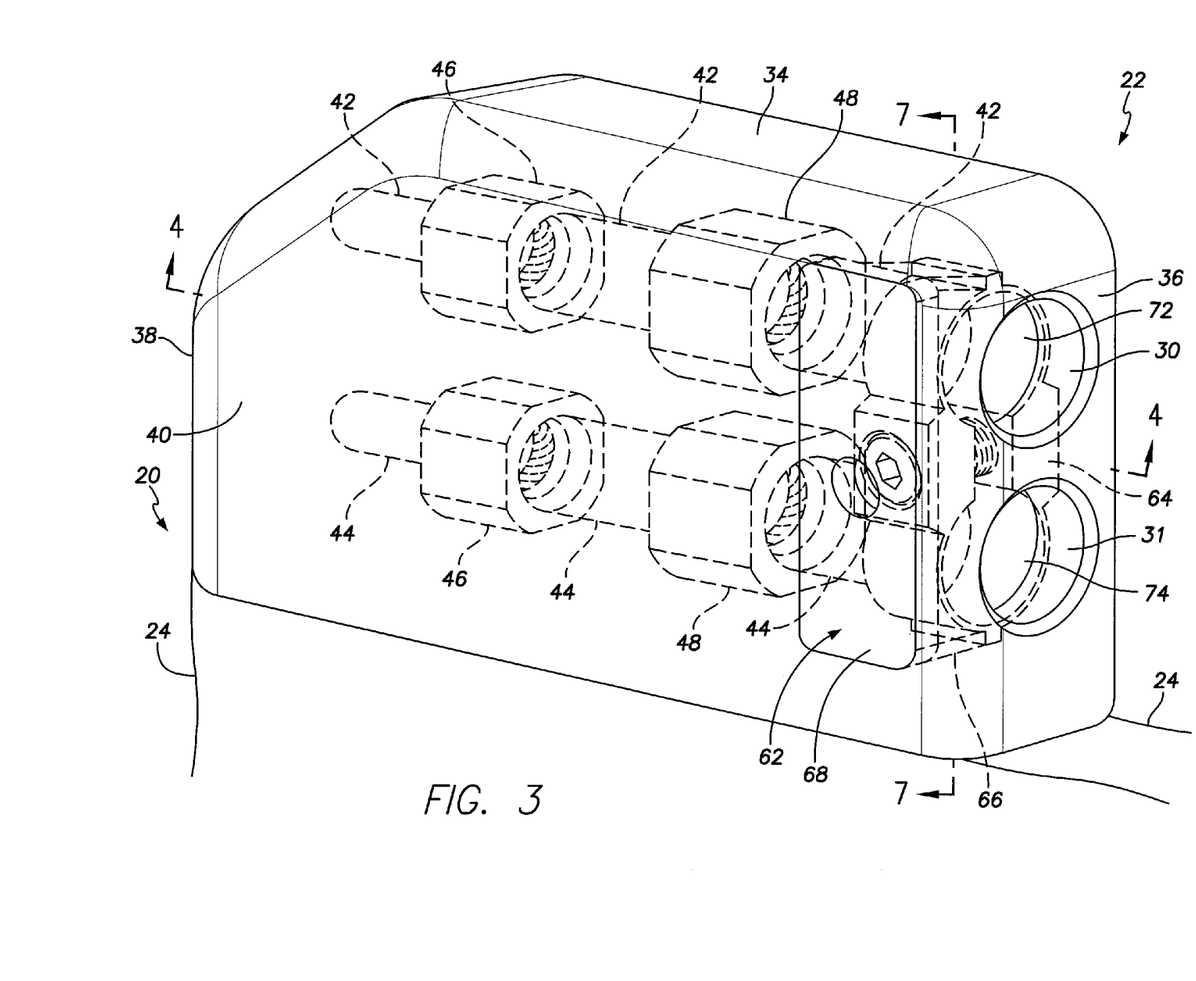
FIG. 3 depicts an enlarged isometric view of the connector assembly of the pulse generator of FIG. 2, except the connector assembly is a version having a single pair of receptacles as opposed to two pair of receptacles.

FIG. 3 depicts an enlarged isometric view of the connector assembly 22 of the pulse generator 20 of FIG. 2, except the connector assembly 22 is a version having a single pair of receptacles as opposed to two pair of receptacles. The connector assembly 22 includes a body 34 with a front or receptacle side 36, a rear side 38 and lateral sides 40 extending generally parallel to each other between the front side 36 and the rear side 38. As can be understood from FIG. 3 and FIG. 4, which is a longitudinal cross-sectional elevation of the connector assembly 22 as taken along section line 4-4 in FIG. 3, the receptacles 30 and 31 are defined in the front side 36 and extend as generally parallel bores 42 and 44 through the body 38 of the connector assembly 22. As best understood from a comparison of the bores 42 and 44 depicted in FIG. 4 and the stepped cylindrical shape of the proximal lead end portion 10 illustrated in FIG. 1, the bores have a stepped cylindrical shape that is configured to matingly receive the proximal lead portion 10.

Figure 4:
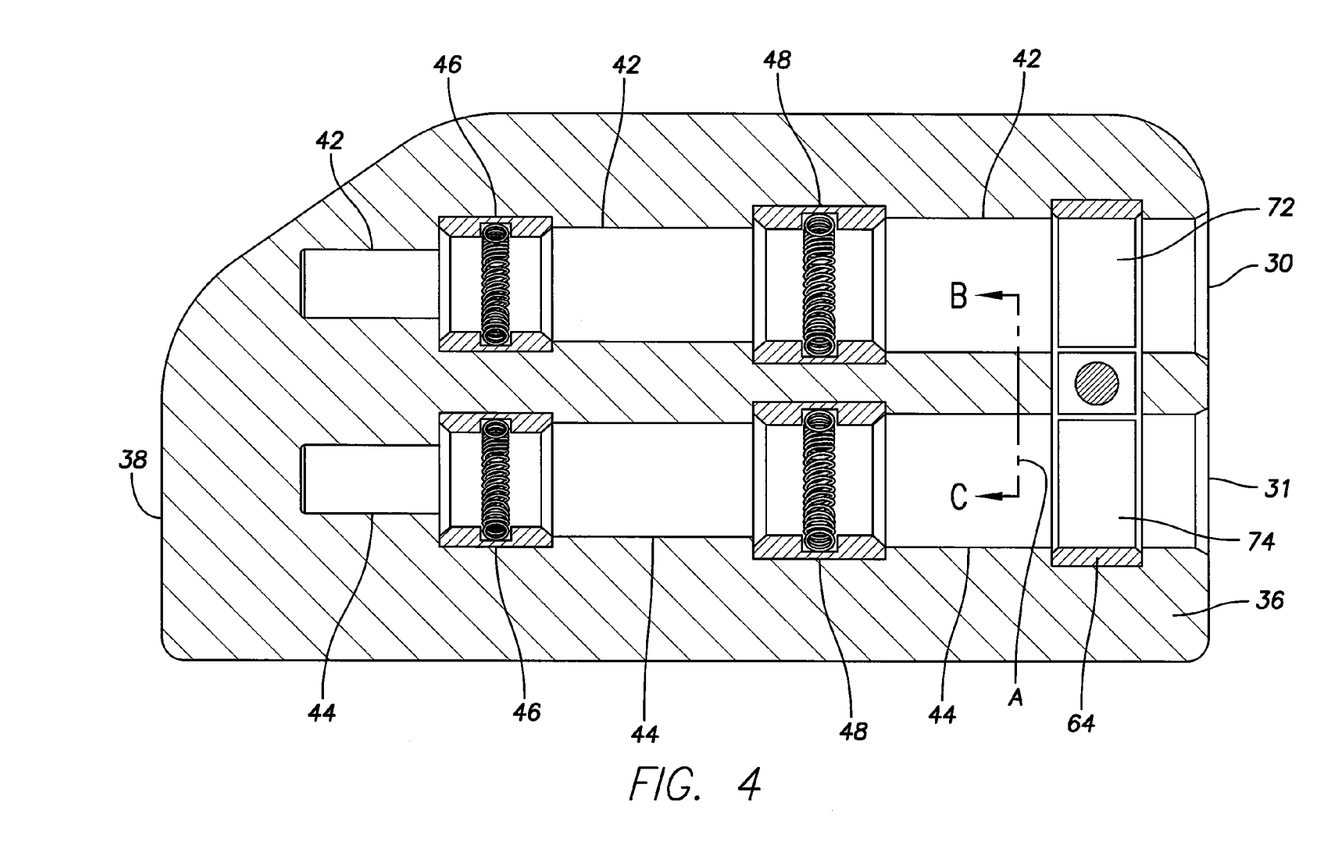
FIG. 4 is a longitudinal cross-sectional elevation of the connector assembly as taken along section line 4-4 in FIG. 3.

As shown in FIGS. 3 and 4, each bore includes a most inward conductive garter spring contact 46 or other resilient electrical contact element and a most outward conductive garter spring contact 48 or other resilient electrical contact element. As can be understood from a comparison of FIG. 4 to FIG. 1, when the proximal lead end portion 10 is received in one of the bores 42 and 44, the tip terminal 12 is received by the most inward contact 46, and the ring terminal 14 is received by the most outward contact 48. Also, the most distal seal ring 16 is located generally inward of line A, as indicated by arrows B and C, when the lead connector end 10 is fully received in the bore 42 or 44 of a receptacle 30 or 31.

Figure 5:
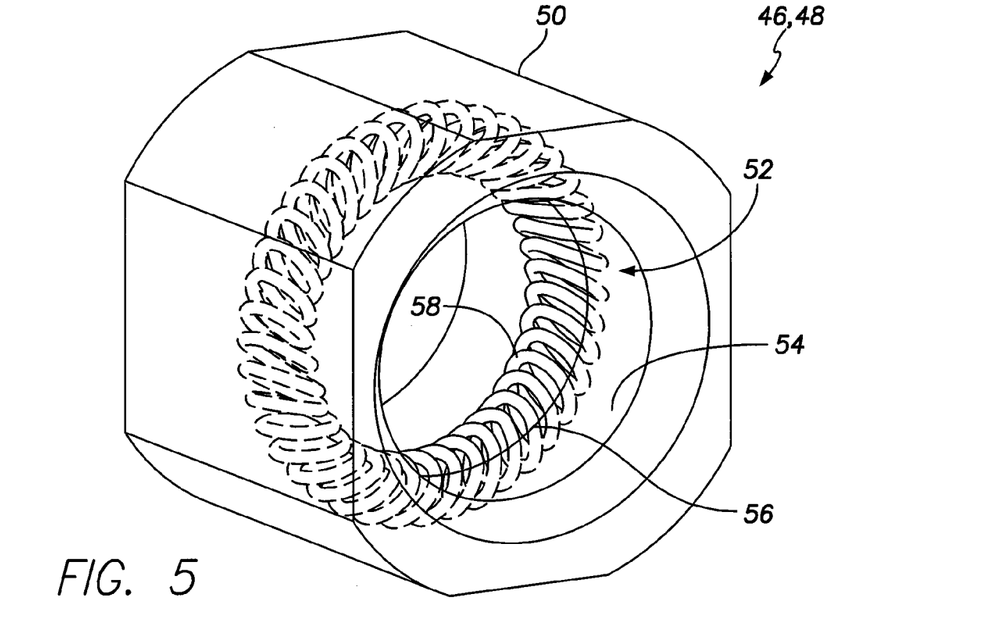
FIG. 5 is an isometric view of one of the garter spring contacts depicted in FIG. 3.
Figure 6:
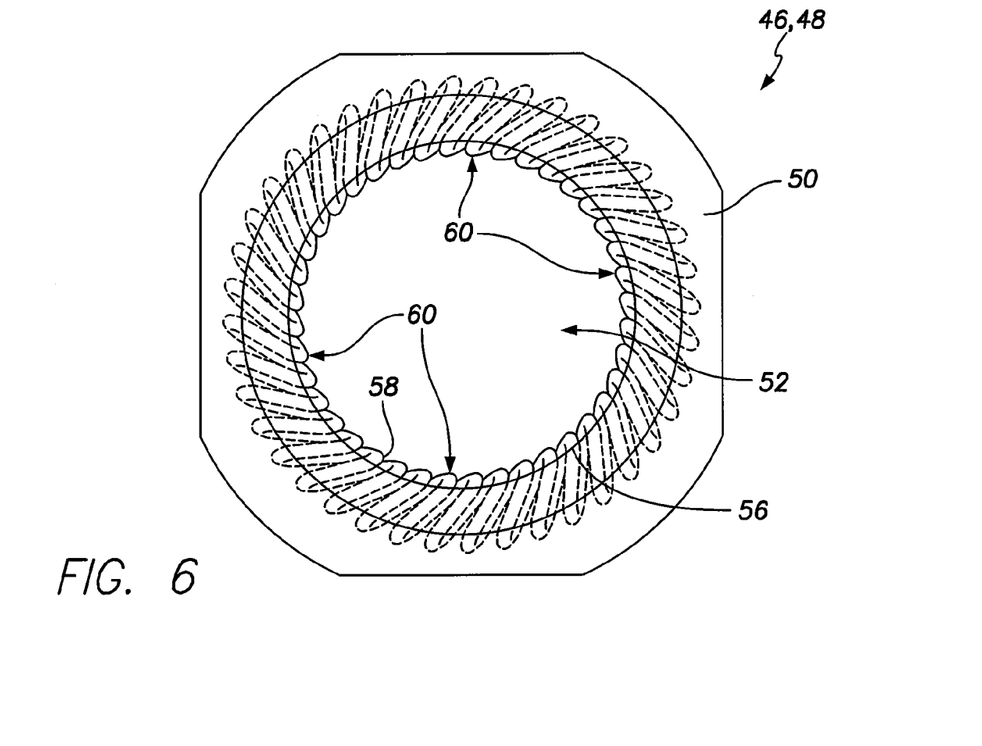
FIG. 6 is an end view of the garter spring contact of FIG. 5.

FIG. 5 is an isometric view of one of the garter spring contacts 46 and 48, and FIG. 6 is an end view of the garter spring contact. The garter spring contact includes a ring or donut-like housing 50 that includes a bore 52 that defines an inner circumferential surface 54. A trough or groove 56 is defined in the inner circumferential surface 54 and is oriented generally perpendicular to a center axis of the bore 52. A canted or slanted helical spring 58 is located in the groove 56 to extend along the entire circumferential length of the groove 56. The spring 58 is at least partially recessed in the groove 56 such that the inner circular boundary 60 of the spring 58 protrudes into the bore 52 past the inner circumferential surface 54, this protruding portion of the spring 58 being exposed for contact with a corresponding electrical contact 12 or 14 of the lead connector end 10 when the end 10 is fully received in it receptacle 30 or 31 and corresponding bore 42 or 44.

In one embodiment of the garter spring contacts 46 and 48, the spring 58 is formed of stainless steel, MP35N, platinum-iridium alloy, or other electrically conductive materials. The housing 50 is formed of formed of stainless steel, titanium, MP35N, or other electrically conductive materials. The garter spring contacts 46 and 48 are electrically connected via feedthru conductors and a feedthru to the electrical components housed within the can 24.

Figure 7:
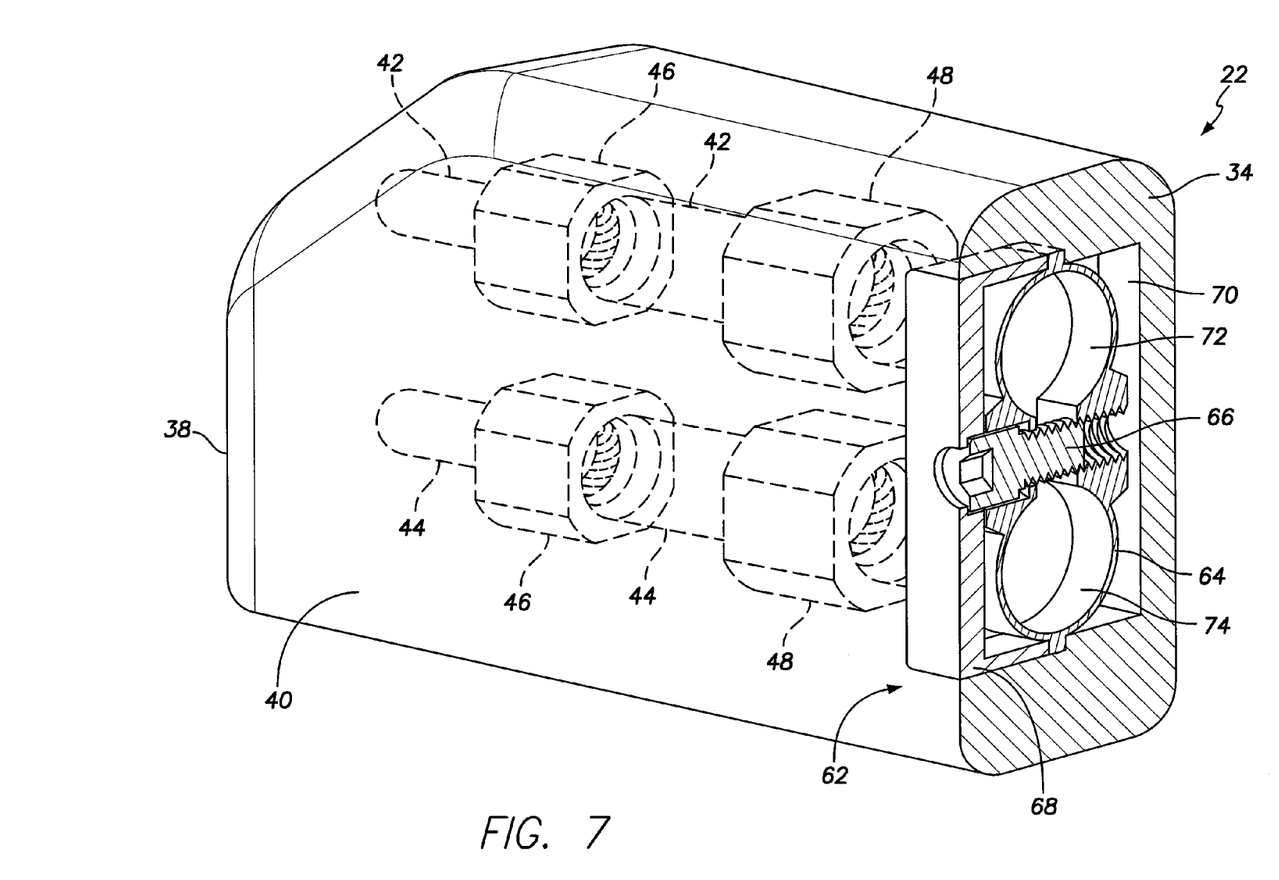
FIG. 7 is an isometric transverse cross-sectional elevation of the connector assembly as taken along section line 7-7 in FIG. 3.
Figure 8:
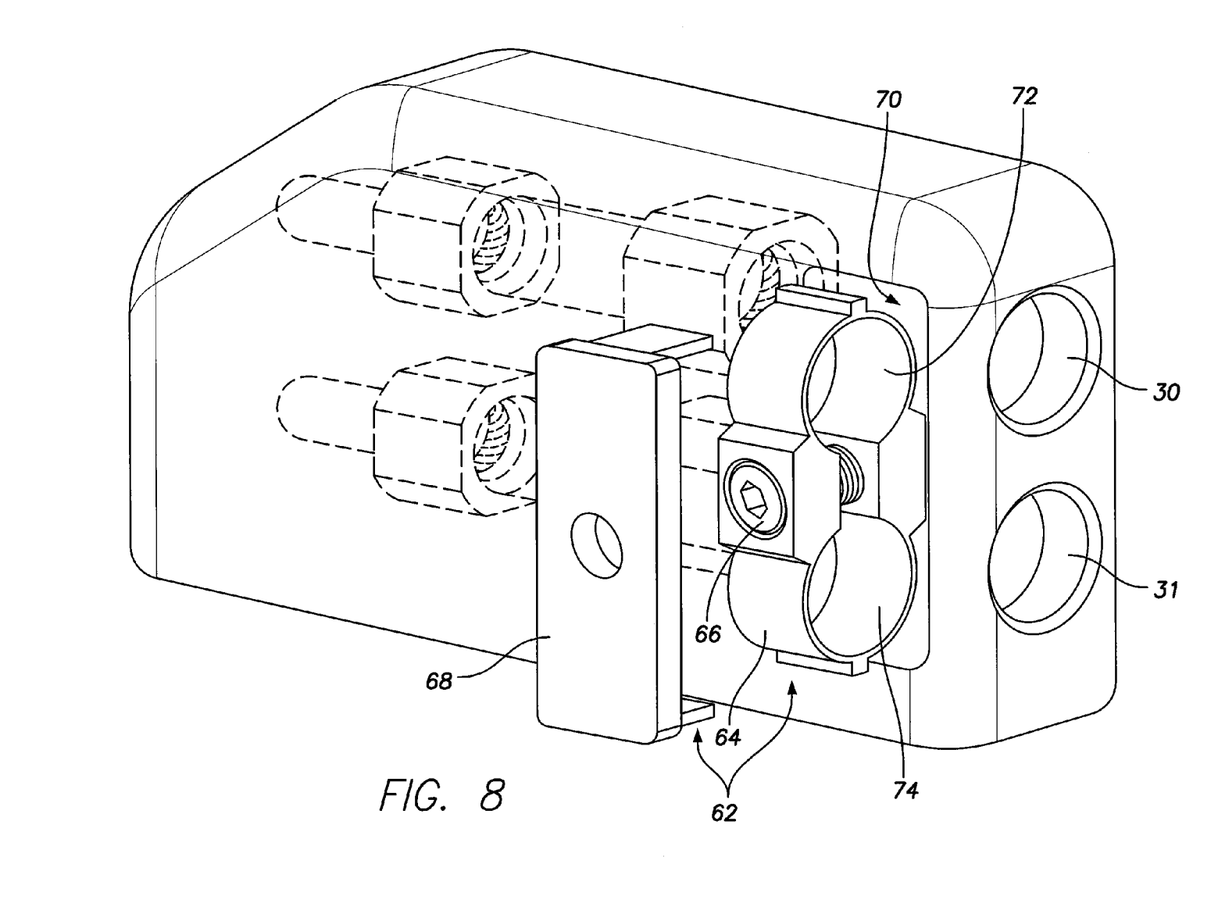
FIG. 8 is the same view of the connector assembly as depicted in FIG. 3, except the retainer assembly is partially exploded from the body.

As indicated in FIG. 3, a retainer system 62 is located in the body 34 just inward of the front side 36 of the body 34. FIG. 7 is an isometric transverse cross-sectional elevation of the connector assembly 22 as taken along section line 7-7 in FIG. 3. FIG. 8 is the same view of the connector assembly 22 as depicted in FIG. 3, except the retainer assembly 62 is partially exploded from the body 34. As shown in FIGS. 7 and 8, the retainer assembly 62 includes a collar portion or clamp portion otherwise referred to herein as a retainer 64, a lock screw 66, and a cover plate 68. The retainer 64 and lock screw 66 may be made of DELRIN®, polyetheretherketone ("PEEK"), ENDOLIGN™ composite or metal such as Titanium, MP35N, 316I stainless steel, etc. The retainer assembly 62 is located in a boxed chamber 70 defined in the body 34. The bores 42 and 44 and the receptacles 30 and 31 open into the boxed chamber 70.

As will be discussed in detail below, in one embodiment, the retainer 64 includes a pair of collars, rings, or collar rings 72 and 74 that are coaxially aligned with respective bores 42 and 44 and receptacles 30 and 31. Thus, as can be understood from a comparison of FIGS. 1 and 4, when lead connector ends 10 are fully received in the bores 42 and 44 such that the pin contacts 12 are in electrical contact with the springs 58 of the most inward garter spring assemblies 46, the ring contacts 14 are in electrical contact with the springs 58 of the most outward garter spring assemblies 48, and the most distal or outward seals 16 are inward of line A in FIG. 4, the rings 72 and 74 can be caused to clamp about the bodies of the lead connector ends 10 distal of the most distal seals 16. Since the rings 72 and 74 engage the lead connector end bodies distal of the most distal seals, there is no need for the retainer system 62 to have a sealing arrangement to isolate the retainer system 62 from body fluids. Specifically, the retainer system 62 does not need to have a septum over the wrench engagement end of the lock screw, thereby avoiding the troublesome issues that arise with the use of a septum.

Figure 9:
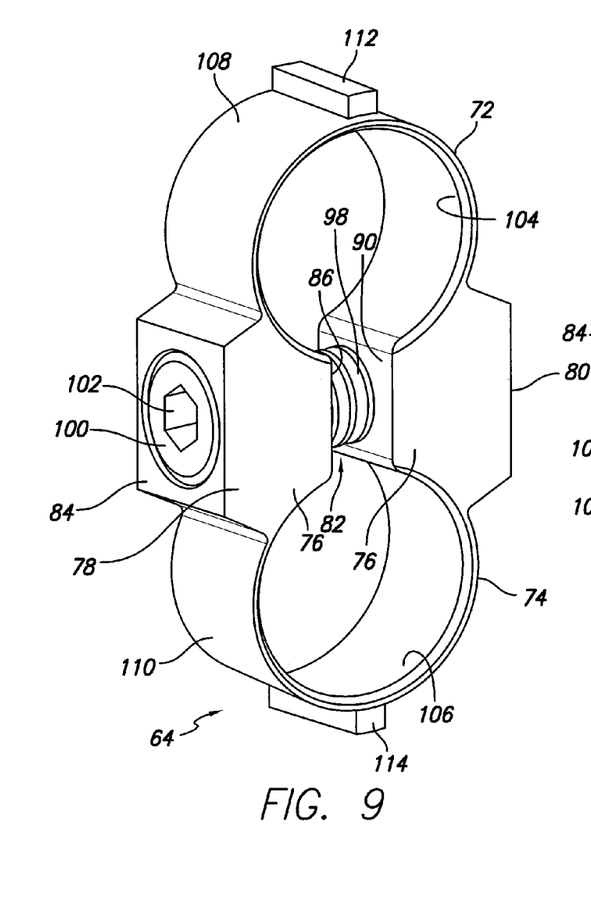
FIG. 9 is an isometric view of the full retainer.
Figure 10:
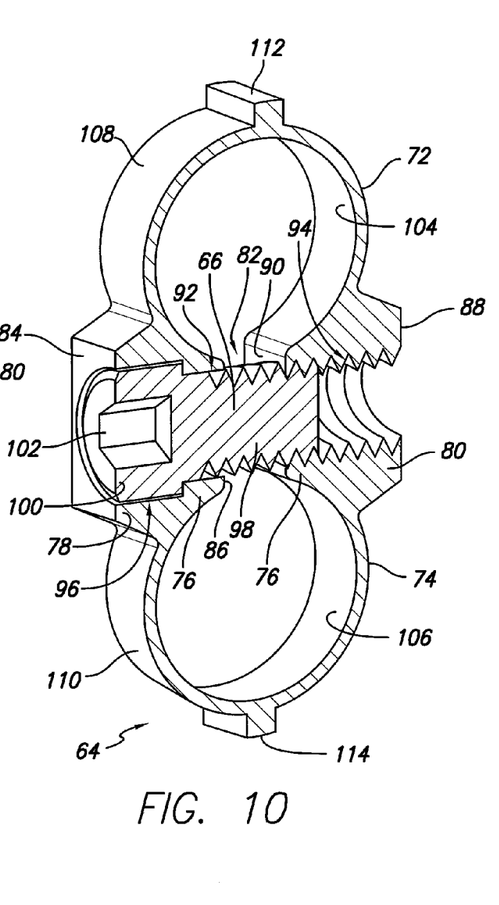
FIG. 10 is the same isometric view as FIG. 9, except illustrated as a transverse cross sectional elevation.

FIGS. 9 and 10 are, respectively, an isometric view of the full retainer 64 and the same isometric view, except illustrated as a transverse cross sectional elevation. As shown in FIGS. 9 and 10, in one embodiment, the retainer 64 is a unitary body including an upper collar ring 72 joined to a lower collar ring 74 via a bridge 76, which includes a first side 78 and a second side 80 separated by a gap 82. The first side 78 includes an outer face 84 and an inner face 86 opposite the outer face 84 and defining a first side of the gap 82. Similarly, the second side 80 includes an outer face 88 and an inner face 90 opposite the outer face 86 and defining a second side of the gap 82 opposite the inner face 86 of the first side 78.

A smooth or non-threaded bore 92 extends through the first side 78 between the outer face 84 and inner face 86, and a threaded bore 94 extends through the second side 80 between the outer face 88 and inner face 90. The bores 92 and 94 are axially aligned with each other across the gap 82. The smooth bore 92 in extending from the inner face 86 of the first side 78 towards the outer face 84 of the first side 78 transitions into a countersunk recess 96 that daylights at the outer face 84. The threaded bore 94 daylights at both the inner face 90 and outer facer 88 in extending through the second side 80.

The threaded lock screw 66 includes a threaded shaft 98 that extends from a head 100 having a tool engagement feature 102 such as, for example, an Allen wrench hole or a straight or Phillips type screwdriver opening. As can be understood from FIG. 10, because the bores 92 and 94 are axially aligned with each other and there is a countersunk recess 96, when the screw 66 is received in the bores 92 and 94, the threaded shaft 98 of the screw 66 extends through the smooth bore 92 and threadably into the threaded bore 94, the threads of the threaded shaft 98 being in threaded engagement with the threads of the threaded bore 94 and the head 100 of the screw 66 being received in a recessed manner in the countersunk recess 96.

In one embodiment, the rings 72 and 74 are each generally unitary in construction such that each ring 72 and 74 includes a respective inner circumferential surface 104 and 106 that extends in a continuous unbroken manner from each face 86 and 90 of the gap 82. Thus, each ring 72 and 74 has a respective inner circumferential surface 104 and 106 that forms a nearly complete 360 degree ring that is free of breaks along its entire 360 degrees except where the inner circumferential surface 104 and 106 meets the gap 82, which forms a break or gap in each inner circumferential surface 104 and 106.

Figure 11:
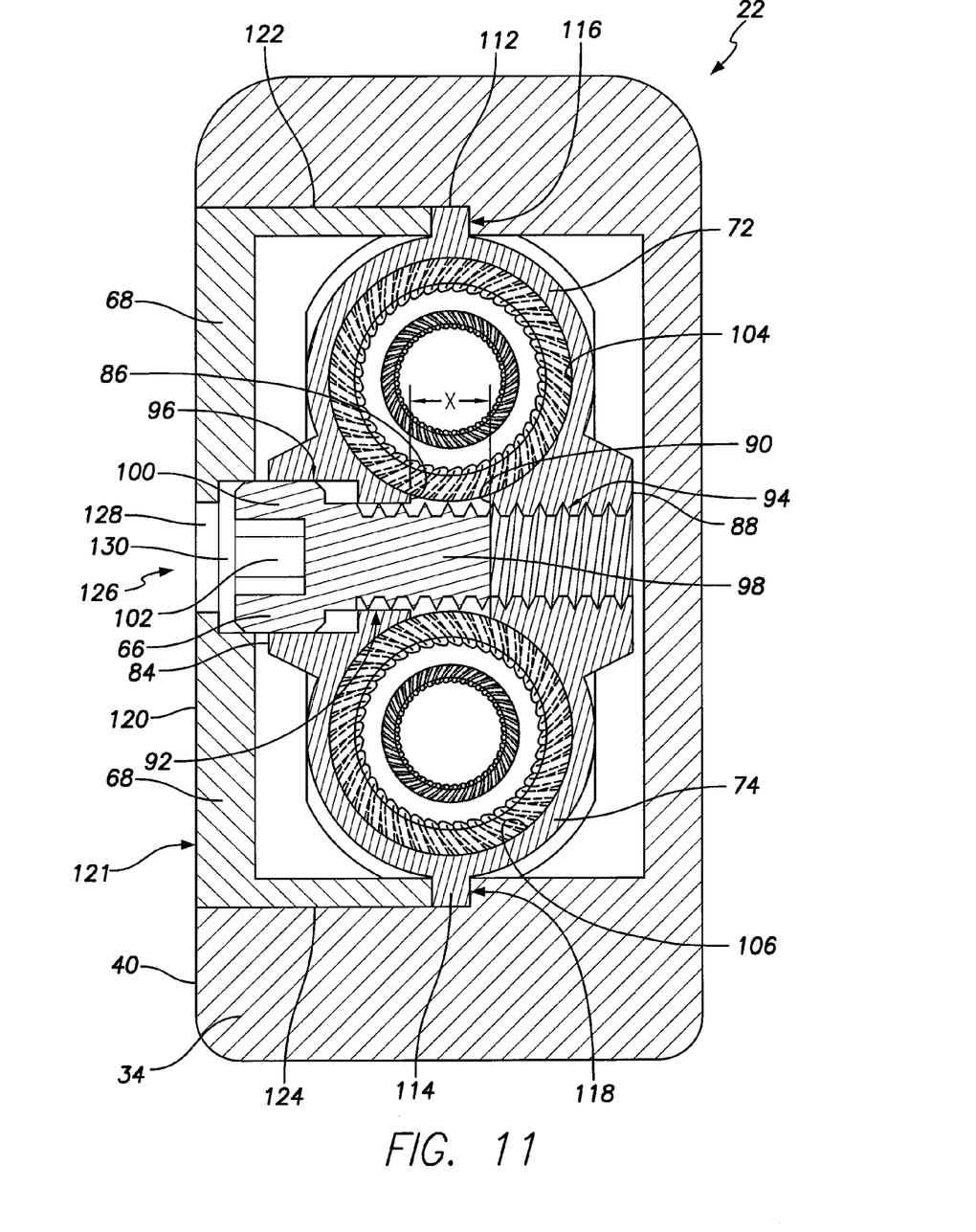
FIGS. 11 and 12 are transverse cross-sectional elevation end views of the connector assembly as taken along section line 7-7 in FIG. 3.
Figure 12:
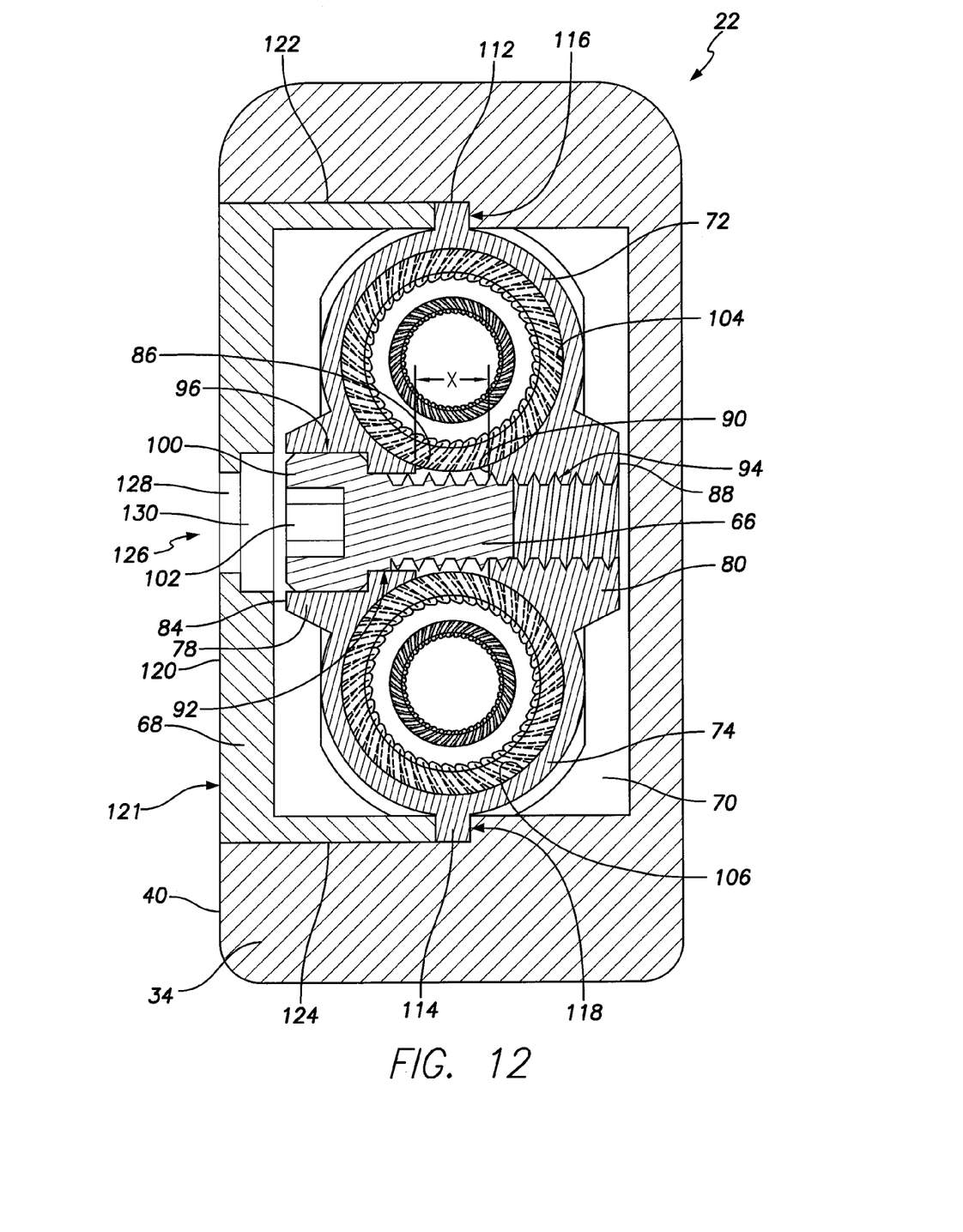

As indicated in FIGS. 9 and 10, the top of the outer circumferential surface 108 of the upper ring 72 and the bottom of the outer circumferential surface 110 of the lower ring 74 each have a respective tab 112 and 114. FIGS. 11 and 12 are transverse cross-sectional elevation end views of the connector assembly 22 as taken along section line 7-7 in FIG. 3. As shown in FIGS. 11 and 12, the tabs 112 and 114 rest against respective ledges 116 and 118 defined in the boxed chamber 70 when the retainer 64 is located in the boxed chamber 70.

As indicated in FIGS. 3, 7, 11 and 12, the cover plate 68 includes an outer plate portion 120 and leg portions 122 and 124 at opposite ends of the outer plate portion 120 and perpendicular to the outer plate portion 120. When cover plate 68 is received in the boxed chamber 70 such that an outer planar surface 121 of the outer plate portion is generally flush with the surface of the lateral side 40 of the body 34, the leg portions 122 and 124 extend inward such that the tabs 112 and 114 are sandwiched between the extreme free ends of the leg portions and the respective ledges 116 and 118.

As illustrated in FIGS. 3, 7, 11 and 12, a tool hole 126 is centered over the engagement feature 102 to allow a wrench or screwdriver to access the engagement feature 102 when the cover plate 68 is seated in place in the boxed chamber 70 over the retainer 64. The tool hole 126 includes a stepped diameter configuration with a narrow diameter outer portion 128 that step-transitions to a larger diameter inner portion 130. The outer diameter portion 128 may have a diameter slightly larger than the diameter of the engagement feature 102 and tool that will be passed through the tool hole 126 into engagement with the engagement feature 102. The inner diameter portion 130 has a diameter generally the same as the diameter of the countersunk recess 96 to allow the screw head 100 to be received in the inner diameter portion 130 when the screw threaded shaft 98 is not threaded into the threaded bore 94, as discussed below.

As can be understood from FIG. 11, when the rings 72 and 74 need to be in an expanded or non-locked down state so as to be able to allow each lead connector end 10 to be inserted into, or withdrawn from, a respective receptacle 30 and 31, the threaded shaft 92 of the lock screw 66 will not be threadably received and otherwise not present in the threaded bore 94, and the screw head 100 will be partially present in the inner diameter portion 130. As a result, the distance X of the gap 82 between the opposed faces 86 and 90 is at its greatest and the diameter of each opening defined by each circumferential surface 104 and 106 of each ring 72 and 74 is at its greatest. The counter bore or inner diameter portion 130 of the cover plate 68 retains the lock screw 66 and keeps the screw 66 in alignment with the bores 92 and 94 when the screw 66 is not threadably engaged within the threaded bore 94, thereby facilitating the screw threaded shaft 98 in threadably reengaging the threaded bore 94 when the retainer 64 needs to be tightened down onto a lead connector end inserted through one of its rings 72 or 74.

As can be understood from FIG. 12, when the rings 72 and 74 need to be in an constricted or locked down state so as to be able to allow lead connector ends 10 to be locked or retained in respective receptacles 30 and 31, the threaded shaft 92 of the lock screw 66 will be threadably received in the threaded bore 94, and the screw head 100 will be fully received in the countersunk recess 96. The more the threaded shaft 92 is threadably received in the threaded bore 94, the more the distance X of the gap 82 between the opposed faces 86 and 90 is reduced and the greater the circumferential locking force of the rings 72 and 74 about each lead connector end received in each respective ring 72 and 74. In other words, the more the threaded shaft 92 is threadably received in the threaded bore 94, the smaller the diameter of each opening defined by each circumferential surface 104 and 106 of each ring 72 and 74.

As can be understood from FIG. 4, when the proximal lead end portion 10 is fully received in one of the bores 42 and 44 such that the tip terminal 12 is received by the most inward contact 46 and the ring terminal 14 is received by the most outward contact 48, the retainer 64 clamps about the lead connector end body distal of the most distal seal ring 16. Thus, the retainer 64 locks about the lead connector end 10 outside the seal zone, which is proximal (located inward) of line A, as indicated by arrows B and C, when the lead connector end 10 is fully received in the bore 42 or 44 of a receptacle 30 or 31.

The retainer system 62 disclosed herein is advantageous for a number of reasons. For example, the retainer system engages the lead connector end outside the seal zone (electrical zone) of the header. As a result, there is no fluid leak path to the electrical contacts in the header and there is no need for a septum over the screw head of the lock screw. Because the arrangement of the retainer system with its generally planar cover plate, there is no fish-eye protrusion associated with the lock screw and, as a result, no associated patient discomfort. The counter bore in the cover plate helps to retain and align the lock screw to facilitate threading of the threaded screw shaft into the threaded bore. The retainer applies a radial force to the lead connector end, which keeps the lead connector end concentric to the receptacle or bore and maintains the full function of the seals by not pushing the seal against one side of the receptacle of the header. Finally, only a single locking screw needs to be acted upon to lock or free two lead connector ends relative to the header.

Although the present invention has been described with reference to preferred embodiments, persons skilled in the art will recognize that changes may be made in form and detail without departing from the spirit and scope of the invention.

What is claimed is:

1. An implantable medical pulse generator for administering electrotherapy via an implantable medical lead having a lead connector end on a proximal end of the lead, the pulse generator comprising:
 a can;
 electrical components disposed within the can;
 a header coupled to the can and comprising:
  a first lead connector end receiving receptacle, the first receptacle having a bore;
  a contact disposed within the bore;
  a housing surrounding the contact, the housing electrically coupled to the contact;
  a feedthru conductor connected to the housing to electrically couple the contact to the electrical components disposed within the can;
  a retainer configured to secure the lead connector end within the first receptacle, the retainer comprising a member and a first collar, the first collar being coaxially aligned with the first receptacle and comprising an inner circumferential surface and a gap in the inner circumferential surface, the inner circumferential surface extending generally continuous and unbroken between a first face of the gap and a second face of the gap, the member being configured such that acting on the member causes a gap distance between the first face of the gap and second face of the gap to decrease, thereby reducing an inner circumferential diameter of the first collar; and a retainer cover having a counter bore providing access to the member, said counter bore sized smaller than the member so as to retain the member in the header
  a seal zone at the first receptacle, the seal zone comprising a region in the bore configured to form a seal with seal rings of the lead connector end of the lead, the seal zone disposed proximal and coaxial to the first collar.

2. The pulse generator of claim 1, wherein the first collar is a unitary body.

3. The pulse generator of claim 1, wherein the member includes a threaded lock screw.

4. The pulse generator of claim 3, wherein the first face of the gap includes a non-threaded bore and the second face of the gap includes a threaded bore, the bores being axially aligned with each other and the threaded lock screw extending through the non-threaded bore and configured to threadably engage the threaded bore.

5. The pulse generator of claim 4, wherein the retainer cover counter bore is axially aligned with the non-threaded bore on an end of the non-threaded bore opposite the first face of the gap, the counter bore configured such that the counter bore maintains alignment of the threaded lock screw with the threaded bore when the threaded lock screw is not threadably engaged with the threaded bore.

6. The pulse generator of claim 1, wherein the header further comprises a second lead connector end receiving receptacle and the retainer further comprises a second collar like the first collar, the second collar being coaxially aligned with the second receptacle and having the gap in common with the first collar such that acting on the member causes the gap distance between the first face of the gap and second face of the gap to decrease, thereby generally simultaneously reducing the inner circumferential diameter of the first collar and an inner circumferential surface of the second collar.

7. The pulse generator of claim 6, wherein the first collar and second collar form a unitary construction.

8. The pulse generator of claim 1, wherein the retainer is located in a region of the header that will result in the retainer being exposed to body fluids when the pulse generator is implanted in a patient.

9. An implantable medical pulse generator comprising:
 a can;
 electrical components disposed within the can; and
 a header coupled to the can and comprising:

a first lead connector end receiving receptacle, the first receptacle having a first bore;

a second lead connector end receiving receptacle, the second receptacle having a second bore;

a first contact disposed within the first bore, a first housing surrounding the first contact, the first housing electrically coupled to the first contact, and a first feedthru conductor connected to the first housing to electrically couple the first contact to the electrical components disposed within the can;

a second contact disposed within the second bore, a second housing surrounding the second contact, the second housing electrically coupled to the second contact, and a second feedthru conductor connected to the second housing to electrically couple the second contact to the electrical components disposed within the can;

a retainer comprising a member, a first collar, and a second collar, the first collar being coaxially aligned with the first receptacle and the second collar being coaxially aligned with the second receptacle, the first collar and the second collar coupled together and sharing a common gap in an inner circumferential surface of each collar, the inner circumferential surface of each collar extending generally continuous and unbroken between a first face of the gap and a second face of the gap, the member being configured such that acting on the member causes a gap distance between the first face of the gap and second face of the gap to decrease, thereby reducing an inner circumferential diameter of each collar; a retainer cover having a counter bore providing access to the member, said counter bore sized smaller than the member so as to retain the member in the header a first seal zone at the first receptacle, the first seal zone comprising a region in the bore configured to form a seal with seal rings of a lead connector end of first lead, the first seal zone disposed proximal to the first collar; and a second seal zone at the second receptacle, the second seal zone comprising a region in the bore configured to form a seal with seal rings of a lead connector end of second lead, the second seal zone disposed proximal and coaxial to the second collar.

10. The pulse generator of claim 9, wherein the first collar and second collar are part of a unitary body.

11. The pulse generator of claim 9, wherein a center axis of an opening defined by the first collar is generally parallel to a center axis of an opening defined by the second collar.

12. The pulse generator of claim 9, wherein the member includes a threaded lock screw configured to extend across the gap when being acted on to cause the gap distance to decrease.

13. The pulse generator of claim 12, wherein the retainer cover counter bore receives an end of the threaded lock screw when the threaded lock screw is not in a condition to decrease the gap, the counter bore maintaining the threaded lock screw in an alignment that allows the threaded lock screw to decrease the gap.

* * * * *